United States Patent [19]

Gerard de Grooth et al.

[11] Patent Number: 5,017,497

[45] Date of Patent: May 21, 1991

[54] PARTICLE DISCRIMINATOR AND METHOD

[75] Inventors: Bernard Gerard de Grooth; Jan Greve, both of Oldenzaal; Leonardus W. M. M. Terstappen, Enschede, all of Netherlands

[73] Assignee: Sequoia-Turner Corporation, Mountain View, Calif.

[21] Appl. No.: 327,416

[22] Filed: Mar. 20, 1989

Related U.S. Application Data

[63] Continuation of Ser. No. 31,478, Mar. 27, 1987, abandoned.

[30] Foreign Application Priority Data

Apr. 21, 1986 [NL] Netherlands .................. 8601000

[51] Int. Cl.$^5$ ............... G01N 33/48; G01N 21/00
[52] U.S. Cl. ............................ 436/63; 356/337; 356/339; 356/39; 250/461.2
[58] Field of Search .................. 356/36–42, 356/335–340; 436/63, 805, 171, 172, 164; 364/500, 554, 555; 422/68; 250/461.2

[56] References Cited

U.S. PATENT DOCUMENTS

| | | | |
|---|---|---|---|
| 4,325,706 | 4/1982 | Gershman et al. | 436/63 |
| 4,435,507 | 3/1984 | Stenkvist | 436/63 |
| 4,455,376 | 6/1984 | Maines | 436/63 |
| 4,492,752 | 1/1985 | Hoffman et al. | 356/39 |
| 4,581,334 | 4/1986 | Kirchanski et al. | 436/63 |
| 4,585,736 | 4/1986 | Dolbeare et al. | 436/63 |
| 4,596,035 | 6/1986 | Gershman et al. | 382/6 |
| 4,599,307 | 7/1986 | Saunders et al. | 356/39 |
| 4,661,913 | 4/1987 | Wu et al. | 436/63 |
| 4,662,742 | 5/1987 | Chupp | 356/39 |

Primary Examiner—Thomas Wallen
Attorney, Agent, or Firm—James J. Farrell

[57] ABSTRACT

Method and apparatus for analyzing particles based on different depolarizing structure associated with the different particle types. Cells in a flow cytometer are illuminated with a linearly polarized light, producing scattered depolarized light whose intensity range, at a selected measuring angle, and in a suitable discriminating space, is used to analyze different particle types.

10 Claims, 6 Drawing Sheets

- • NEUTROPHILS
- × EOSINOPHILS
- □ MONOCYTES
- ○ LYMPHOCYTES
- △ MICROSPHERES
- --- IDEAL SPHERES

PARTICLE DISCRIMINATOR AND METHOD

This application is a continuation, of application Ser. No. 07/031,478, filed 27 Mar. 1987 now abandoned.

FIELD OF THE INVENTION

The present invention relates to particle discrimination by light scattering, and more particularly, to a method and flow-cytometer apparatus for discriminating particles on the basis of different light-scattering depolarizing structures.

REFERENCES

Benson, M. C., et al., Cytometry, 5:515-522 (1984).
Hoffman, R. A., et al., Proc. Nat. Acad. Sci. USA, 77:4914 (1980).
Hulst van de, H. D., Light Scattering by Small Particles, Dover Publications, Inc., New York, 1981.
Julius, M. H., et al., in Mammalian Cells: Probes and Problems (Richmond, C. R., et al., eds.), ERDA Symposium Series CONF-731007. Technical Information Center, Oak Ridge, Tennessee, 1975, p. 107.
Hoffman, R. A., et al. Proc. Nat. Acad. Sci. USA, 77:4914 (1980).
Loken, M. R., et al., Ann. N.Y. Acad. Sci., 254:163-171 (1975).
Marston, P. L., J. OPt. Soc. Am. 73:1816-1819 (1983).
Mullaney, P. F., et al., Biophys J. 10:764-772 (1970).
Salzman G. C. et al., Acto. Cytol. 19:374-377 (1975).
Terstappen, L. W. M. M., et al., Cytometry, 7:178-183 (1986).
Terstappen, L. W. M. M., et al., J. Immunol. Methods, 95:211 (1986).
Terstappen, L. W. M. M., et al., Cytometry, 6:316-320 (1985).
Visser, J. W., et al., Blood Cells, 6:391-407 (1980).
Weil, G. J., et al., Blood, 57:1099 (1981).

BACKGROUND OF THE INVENTION

Particle discrimination methods are useful in a variety of clinical assays, such as in determining the number and types of cells in a blood sample, detecting bacterial or virus particles in a body fluid sample, and assaying cell volumes and density, e.g., sperm count. Detection of non-cellular particles, such as uric acid crystals in a urine sample, is also valuable in certain clinical tests. Analysis of crystals and other particles in fluid suspension also has important industrial uses.

One method which allows rapid and efficient particle discrimination in a particle-suspension sample is flow cytometry. In this method, a suspension of particles, typically cells in a blood sample, is transported through a flow chamber where the individual particles in the sample are illuminated with one or more focused light beams. The interaction of the light beam(s) with the individual particles flowing through the chamber is detected by one or more light detectors. Commonly, the detectors are designed to measure light absorption or fluorescence emission, at specific beam or emission wavelengths, and/or light scattering at specific scattering angles. Thus each particle that passes through the flow chamber can be characterized as to one or more features related to its absorption, fluorescence, light scattering or other optical or electrical properties. The one or more properties which are measured by the detectors allow each particle to be mapped into a feature space whose axes are the light intensities or other properties which are measured by the detectors. In the ideal, the different particles in the sample map into distinct and non-overlapping regions of the feature space, allowing each particle to be analyzed based on its mapping in the feature space. Such analysis may include counting, identifying, quantifying (as to one or more physical characteristics) and/or sorting of the particles.

Two general types of light scattering measurements are routinely made in flow cytometry. Light intensity measurements made at small angles (about 1.5°-13° with respect to the incident light beam), usually called forward or small-angle scattering, give information on cell size (Mullaney). Forward scattering also strongly depends on the difference of refraction between cells and the extracellular medium, so that cells with a damaged membranes, for example, can be distinguished. Light intensity measurements made at an angle of about 65°-115° from the incident light, usually referred to as orthogonal light scattering, and these provide information about the size and degree of structuredness of particles (Visser). As an example, the inventors and co-workers have recently shown that human cytotoxic lymphocytes appear to have different structural characteristics than regulatory and B-lymphocytes, based on the greater orthogonal light scattering intensities of the cytotoxic cells (Terstappen). If the width of the illumination beam is smaller than the diameter of the particles, the pulse shape of the light at orthogonal scattered angles yields information about the length and shape of the cells.

Simultaneous light scattering measurements at different angles or in combination with absorption or fluorescence measurements have been proposed in flow cytometry methods. Simultaneous measurement of forward and orthogonal light scattering can be used to discriminate cytotoxic lymphocytes from regulatory and B-lymphocytes as indicated above (Terstappen), and lymphocytes from other peripheral leukocyte cells (Hoffman). Absorption of light in combination with light scattering is used in flow cytometry to distinguish between erythrocytes and thrombocytes, and between lymphocytes, monocytes, basophilic granulocytes, eosinophilic granulocytes, and neutrophilic granulocytes (Technicon Hemalog or H1 systems). However, this method requires staining the cells, and is therefore rather complex and may preclude using the cells for further study after cell sorting.

Light scattering measurements combined with circular dichroism (CD) and optical rotatory dispersion (ORD) also have the potential for particle discrimination in suspensions of virus particles or cells. Studies of the effect of Mie (isotropic particle) scattering on the CD and ORD spectra of DNA in viral particles (Gordon, 1972; Gordon, 1974) suggest that scattering measurements can be used to correct ORD and CD measurements in larger biological structures, such as virus particles and cells, to allow particle discrimination on the basis of characteristic ORD and CD characteristics. Differential scattering of right and left circularly polarized light, for discrimination of a number of different microorganisms, has been demonstrated (Salzman). The circular intensity differential scattering (CIDS) method is like CD, which exploits the differential absorption of left and right circularly polarized light, but takes advantage of differential scattering by helical structures, such as DNA, of right and left circularly polarized light.

SUMMARY OF THE INVENTION

It is a general object of the invention to provide a light scattering method which extend the types of particles which can be distinguished in a flow cytometer system.

A more specific object of the invention is to provide such a method for distinguishing particles on the basis of depolarizing structures which are characteristic of the different particle types.

As one exemplary method, it is an object of the invention to provide a method for distinguishing different granulocyte cell types.

Still another object of the invention is to provide apparatus for discriminating particles on the basis of differential depolarizing particle light scattering.

The method of the invention is designed for discriminating two or more different particle types on the basis of different depolarizing structures characteristic of the particle types. In practicing the method, a suspension of particles containing the different particle types is directed through an optical sensing zone, and the particles in the zone are illuminated with an incident beam of linearly polarized light. Each illuminated particle passing through the zone produces depolarized scattered light whose intensity, at a selected scattering angle, is dependent on the particle's depolarizing structure. The intensity of the depolarized scattered light at the selected angle is within an intensity distribution range, in a suitable discriminating/or particle-feature space, which is (a) characteristic of one of the particle types and (b) substantially non-overlapping with the intensity distribution of the other particle type(s) in the suspension. The measured intensity of depolarized scattered light at the selected angle, when evaluated in the discriminating space, allows the different particle types in the suspension to be discriminated. More generally, the method allows for analysis of different particle types, including counting, discriminating, quantifying physical characteristics, and/or sorting the different particle types.

Where the particles can be analyzed (e.g., distinguished) on the basis of depolarization alone, the feature space may be a one-dimensional space defined by the intensity of the depolarized light scattered from the illuminated particles, at the selected angle. More commonly, the particles are analyzed on the basis of depolarization intensity and at least one other optical or electrical response characteristic such as total light scattering, absorption, fluorescence, CD, or ORD, whose mean response values differ for the different particle types. Here the discriminating space is an incremental element defined in one dimension by depolarization scattering intensity and in at least one other dimension, by an incremental change in at least one other particle-measurement parameter, as will be explained further below.

In one exemplary embodiment, the method is used to analyze, and in particular to distinguish, granulocytic eosinophils and neutrophils. Cell discrimination is made in a two-dimensional feature space defined in one dimension by orthogonal depolarized light scattering, and in a second dimension, by total orthogonal scattered light.

The invention further includes apparatus for analyzing at least two different particle types on the basis of different depolarizing structures characteristic of the different particle types. Within a flow cell in the system an optical sensing zone is defined in which particles in suspension are illuminated by a polarized beam of light. The intensity of depolarized scattered light from the particles is measured by a detector at a selected angle, which, in a suitable feature space, allows particle discrimination based on different depolarizing structure. The apparatus includes an analyzer for recording measured cell +parameters, and analyzing particles based on depolarized scattering intensity in a suitable discriminating space.

These and other objects and features of the invention will becomes more fully apparent when the following detailed description of the invention is read in conjunction with the accompanying drawings.

DETAILED DESCRIPTION OF THE INVENTION

I. Cytometer Apparatus

Figure 1:
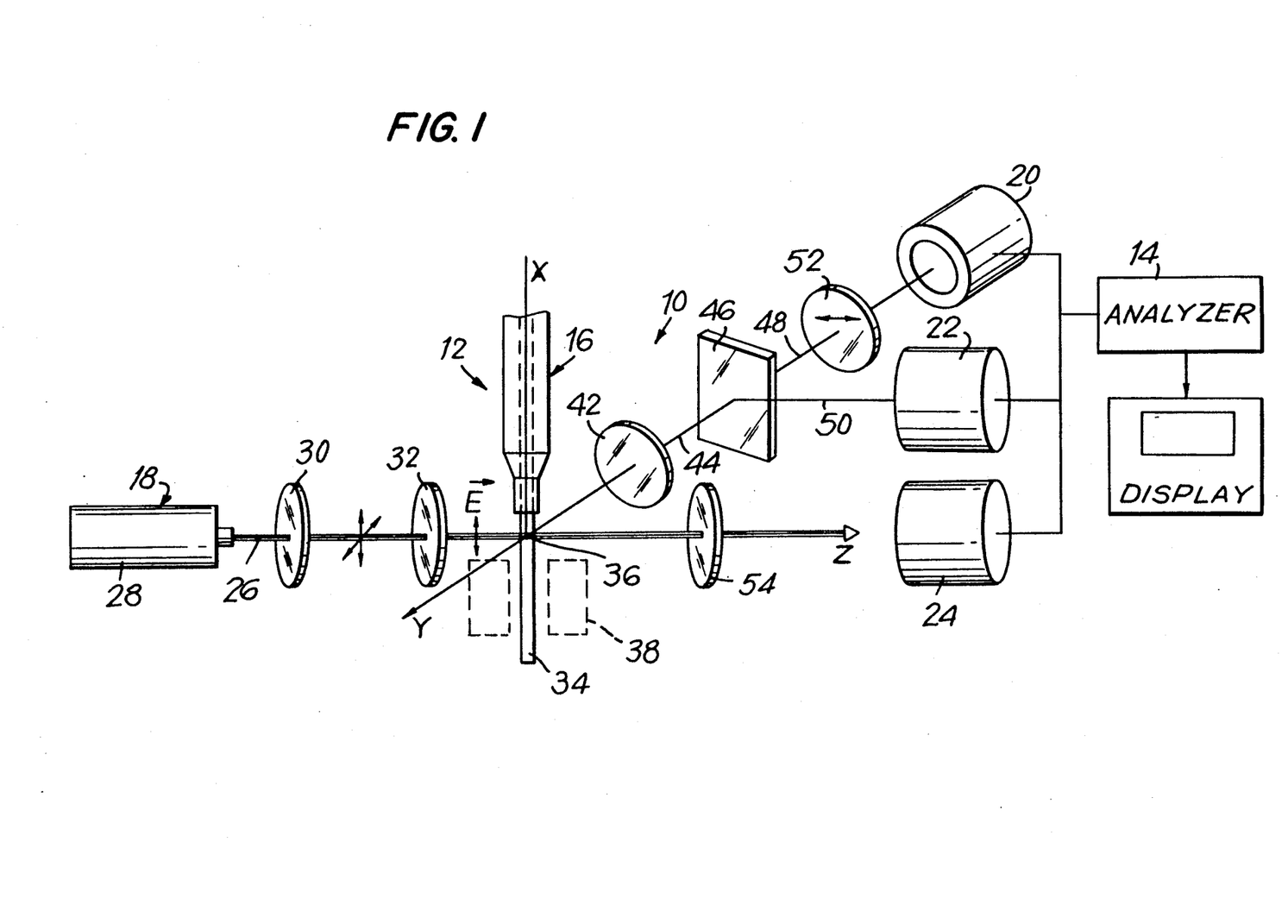
FIG. 1 is a diagramatic illustration of a flow-cytometry light-scattering apparatus of the invention.

Cytometer apparatus constructed for use according to the present invention is shown at 10 in FIG. 1. A flow cytometer 12 in the apparatus is designed for measuring depolarized light scattering from sample particles, as detailed in part A. An analyzer 14 in the apparatus functions to analyze particles in the sample on the basis of one or more optical measurements, including depolarized light scattering, as described in part B. As defined herein, particle analysis according to the method may involve particle counting, discriminating, quantifying (physical parameters), and/or sorting.

A. Flow Cytometer

The basic hardware of the flow cytometer is a flow chamber 16 through which the particles in a suspension sample are transported, a light source 18 for illuminating particles moving through the flow cell, and photodetectors, such as detectors 20, 22, and 24, for measuring optical-response parameters of the illuminated cells.

Light source 18 is designed to illuminate the particles in the flow chamber with a focused, linearly polarized beam of light. The light beam, indicated in the figure at 26, is a beam of coherent light produced by a conventional laser 28. A 3 Watt argon ion laser (Coherent Radiation, Palo, Alto) tuned at 488 nm or a 5 mW helium neon laser (Model 120S, Spectra physics, San Jose, CA) are suitable. The light beam from the laser is focused on the cell stream in the flow cell by a lens 30, which for the above argon laser includes two cylindrical lenses of focal lengths 200 and 20 mm, and in the case of the helium neon laser, is a single spherical lens with focal length 70 mm. Although a source of coherent (laser) light is shown, the light source may alternatively be a conventional arc lamp (incoherent) source whose beam is focused by lens 30.

The light beam may be linearly polarized by means of a polarizing filter 32, such as an HN 7 filter available from Melles Griot (Irvine, CA). Alternatively, laser 28 may be designed to output a linear polarized light beam, such as in the case of a linear polarized Argon laser. For purposes of discussion, the orientation of the polarizing filter is assumed to be such as to produce linearly polarized light whose electric field vector E parallels the x axis in the x-y-z coordinate system shown, where the light beam is directed along the z axis and particles move through the flow cell along the x axis. That is, the polarized electric field vector is aligned with the direction of particle flow. However, it is noted that the light beam may be directed at a range of angles within the x-z plane, typically from about 10 to 170 degress with respect x axis, and that the electric field vector may be polarized in virtually any direction in the x-y plane.

Although not shown here, cytometer 12 may include other light sources for determining a variety of optical parameters in addition to light scattering, such as optical absorption fluorescence, CD, and ORD, as well as an unpolarized light source, or a light polarized in a second direction, for light scattering measurements.

Flow chamber 16 may be a conventional closed optical cell such as a quartz flow cell with a 250 μm × 250 μm square flow channel, available from from Hellma GmbH and Co (Mullheim/Baden, W. Germany). The chamber is arranged to direct particles in a liquid suspension via an injection tube 34 into and through an optical sensing zone 34 where the light scattering measurement is made.

Where the flow cytometer is intended for use in cell sorting, the flow chamber may be a "jet-in-air" type cell which produces a jet of suspension droplets just downstream of the sensing zone. A conventional jet-in-air cell, such as used in fluorescence activated cell sorting, and commercially available (Becton Dickinson, Mt. View, CA) is suitable. Alternatively, cell sorting may be done with a flow channel having a small jewel orifice for droplet formation. The cytometer may additionally include a cell sorter 38 which is operated conventionally to deflect selected particles, based on the optical parameters of the particles measured in the sensing zone, into a collection tube. In addition, a small obscuration bar (not shown) may be placed in front of the orthogonal light detection objective in order to block the laser light scattered by the cylindrical fluid stream. Typically the bar blocks light at an angle between about 87°–93° with respect to the incident light. With such an obscuration bar, the relative contribution of the cross depolarization (discussed below) to the total depolarization is increased. The flow sorting system with obscuration bar has been used successively in cell sorting based on depolarization discrimination, as described below.

According to an important feature of the invention, the cytometer includes at least one optical detector for detecting the intensity of depolarized light scattered by the particles in the sensing zone. As defined herein "depolarized scattered light" is light whose electric field vector contains a significant vector component in the plane normal to the electric field vector of the incident light beam. In the configuration shown, where the incident-light field vector is directed along the x axis, normal to the y-z plane, the field vector of the depolarized scattered light contains a significant component in the y-z plane.

The embodiment of the invention illustrated in the figure is designed for measuring orthogonal depolarized light, i.e., depolarized light which is scattered at an angle between about 65° and 115°, and preferably about 90°, with respect to the direction of the incident beam, i.e., light scattered along the y axis in FIG. 1. As seen in the figure, total orthogonally scattered light is collected by a lens 42 which functions to collimate the scattered light beam, indicated at 44 in the figure. A conventional microscope objective, such as a Leitz H32, NA 0.6 objective, is suitable.

The embodiment shown is also designed to measure total orthogonal scattered light, defined herein as orthogonal scattered light containing both the polarized and depolarized electric field vectors produced by particle scattering of the polarized incident light. A conventional beam splitter 46 in the optical train splits beam 44 into two beams, indicated at 48 and 50, each composed of total orthogonal scattered light. Beam 48 is passed through a polarizer 52 which filters out scattered light polarized along the x axis, and thus passes scattered depolarized light only, i.e., scattered light having a vector component in the z direction in the figure. One suitable polarizer is a polaroid filter HN 7, available from Melles Griot (Irvine, CA).

The intensity of the filtered beam is measured by detector 20, which is preferably a photomultiplier, such as Model R928 photomultiplier commercially available from Hamamatsu (Middlesex, NJ). The photomultiplier is adjusted to gather light from a cone about the y axis whose angle of collected light $\Delta\phi$ can range between about 3°–13°, as will be discussed further below. The cone of light collected by the detector can be adjusted by a diaphragm (not shown) placed in front of lens 42. The voltage level measured by the detector is input analyzer 14 whose operation is described in part B.

The intensity of beam 50, which is composed of total orthogonal scattered light, is measured by detector 22 which is preferably a photomultiplier such as described above. The cone of light which is measured by detector 22 may be adjusted by a diaphragm placed before lens 42, as above. The voltage level signal recorded by the detector is supplied to analyzer 14. It will be recognized that other photodetectors, such as photodiode detectors, may be used for one or both detectors 20, 22, where the intensity of the orthogonal scattered light beams is sufficient.

The cytometer shown in the figure is also designed for measuring the intensity of total forward scattered light, i.e., light scattered at an angle of within about 25 degrees of the axis of the incident light, and preferably within a cone centered on the axis of the incident light. The forward scattered light is collimated by a lens 54. The intensity of the beam is measured by detector 24, which is preferably a photodiode, such as photodiode model pin 10-D, available from United Detector Technology (Hawthorne, CA). The cone of light collected, which can be adjusted by a diaphragm (not shown) placed in front of lens 54, is typically between about 2°–17°. The output of detector 24 is fed to analyzer 14.

It is noted here that the minimum detector hardware needed to measure depolarized scattered light is a single photodetector, such as detector 20, and a polarizing filter passing depolarized scattered light only. Further, although the cytometer shown is designed for measuring orthogonal depolarized scattered light, it is understood that detector 20 may be positioned at any point on the hemisphere bounded by the x-z plane in the figure, provided that the measuring angle provides adequate intensity discrimination between the different particle types being examined. For example, the detector may be placed at an angle between about 90°–180° (for measuring depolarization of back scattered light), at the orthogonal position shown, or at the position of detector 24 (for measuring depolarization of forward scattered light).

One or more additional detectors, such as detectors 22 and 24, provide additional feature information which may be required for discriminating different particle types based on different intensity distributions of depolarized scattered light, as will be considered in part B below. As noted, detectors 22 and 24 in the embodiment of the invention shown in the figure provide information about total scattered light in orthogonal and forward directions, respectively. Other optical detectors, in addition to or in lieu of detectors 22, 24, may provide optical parameter information relating to (a) the intensity of depolarized scattered light at a second scattering angle, (b) the intensity of depolarized or total scattered light at a different conus angle of collected light, (c) light absorption, (d) fluorescence emission, and (e) ORD and CD parameters. The cytometer may also be equipped with non-optical cell detectors, such as Coulter-effect detectors, for measuring cell volume by the resistance or capacitance characteristics of the particles in the flow chamber.

B. Analyzer

The analyzer in the apparatus functions to record and process signal-response information from the one or more detectors, for purposes of analyzing each particle in the suspension as to particle type. In essence, each particle type which is to be analyzed is first characterized as to its range of values, in each dimension, in a one or multi dimension feature space. At least one dimension in the feature space is the range of intensity values of depolarized scattered light, at a selected scattering angle, produced by each of the particle types to be analyzed.

Figure 2:
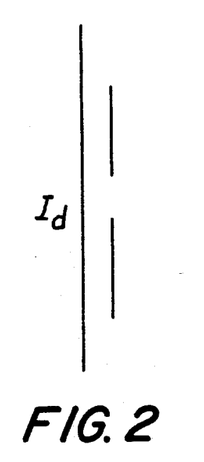
FIG. 2 shows a one-dimensional feature space defined by depolarized light scattering intensity, and non-overlapping intensity distributions of two different particles.

In the simplest case, the different particles in the suspension can be distinguished solely on the basis of depolarization scattering intensity. This case is illustrated in FIG. 2, which shows the range of intensities $I_d$ of depolarized light scattering measured at a selected angle for particles A and B in a particle suspension. The different depolarization intensities of the two particles are related to different depolarizing structures in the two particles, causing different degrees of anisotropic scattering from the particles, as will be considered below.

As seen, each particle has an intensity distribution range, along the $I_d$ axis, which is characteristic of each particle type, and substantially non-overlapping with the intensity distribution of the other particle type.

Figure 3:
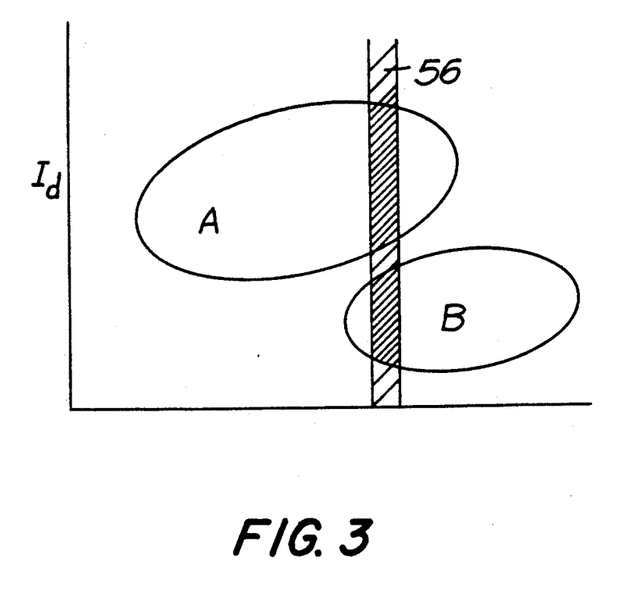
FIG. 3 illustrates a two-dimensional feature space representing, along a vertical axis, depolarization intensities measured for two different particles, and along a horizontal axis, total light scattering intensity.

In many cases, particle analysis may require one or more additional optical or non-optical response measurements in order to separate the distribution of cells, in a multi-parameter feature space, into separate, non-overlapping regions. An example of a particle discrimination based on a two-dimensional feature space (2-parameter density map) is illustrated in FIG. 3. Here the depolarization intensity distribution of the different A and B type particles overlap somewhat on the $I_d$ axis, as indicated, such that particles cannot be mapped positively into one or the other distribution range based solely on this parameter. This overlap is "resolved" when the particles are mapped into regions defined in one dimension by depolarization scattering intensity ($I_d$) and in the second dimension, by total scattering intensity ($I_t$), resulting in two distinct and non-overlapping regions result. Note that the particles cannot be distinguished unequivocally on the basis of total scattering intensity alone, since this parameter gives considerable overlap between the two particle types.

More generally, the two dimensional feature space defines a series of area elements paralleling the $I_d$ axis, such as element 56, defined by an increment in total scattering intensity. Within each such element, which is also referred to herein as a discriminating space, the two particles can be distinguished on the basis of their different depolarization scattering intensities. That is, within each element or discriminating space, the suspension particles produce a depolarizing scattering intensity which is characteristic of one of the particle types, and non-overlapping with the distribution of the other particle type(s) in the suspension.

It can be appreciated that the second parameter used in defining an appropriate feature space must be such as to separate the mappings of the two or more particle types into distinct and non-overlapping regions of the feature space. In the present example, same-angle total light scattering is an effective second parameter because, for each particle type, particles with lower depolarized scattering intensity (B type particles in FIG. 3) tend to show higher total scattering intensity. However, for other particles, it may be desirable or necessary to "resolve" the overlapping $I_d$ intensity distributions with optical or non-optical parameters other than same-angle total scattering.

Figure 4:
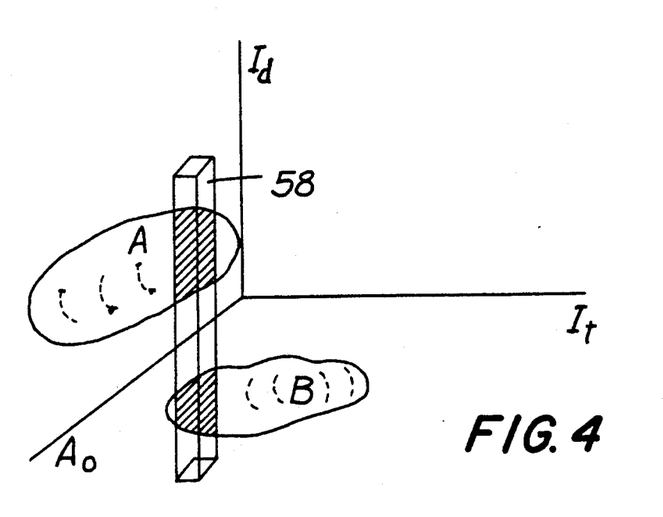
FIG. 4 illustrates a three-dimensional feature space defined by depolarized scattered light in one dimension, total scattered light in a second dimension, and absorbed light in the third dimension.

The expansion of the particle-discriminating method to three dimensions is illustrated in FIG. 4. The different A and B particles are here characterized by their mapping into one of two distinct volume regions defined by the particles' depolarized scattering intensity ($I_d$) in one dimension, total light scattering ($I_t$) in a second dimension and light absorption ($A_O$) in a third dimension. Analogous to the two-dimensional case described in FIG. 3, the three dimensional feature space defines a series of volume elements paralleling the $I_d$ axis, such as element 58, defined by increments in total scattering intensity and absorption. Within each such element (the discriminating space) the two particles can be distinguished on the basis of their different depolarization scattering intensities. That is, within each element, the suspension particles produce a depolarizing scattering intensity which is characteristic of one of the particle types, and non-overlapping with the distribution of the other particle.

Figure 5:
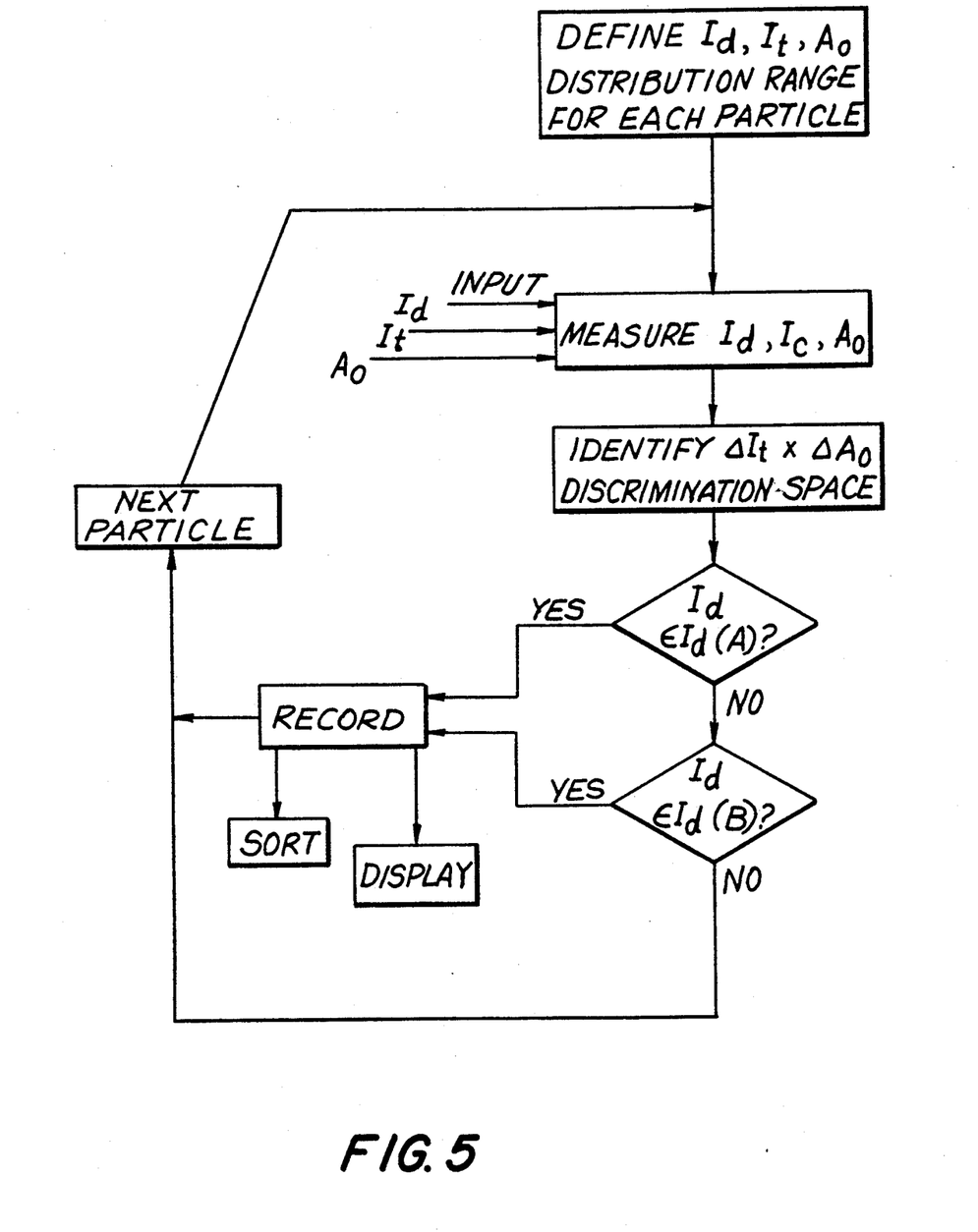
FIG. 5 is a flow diagram of the algorithm used in analyzing particle types, according to the invention.

FIG. 5 is a flow diagram of an algorithm carried out by analyzer 14 for analyzing two particles A and B on the basis of their distribution in the $I_d/I_t/A_O$ feature space illustrated in FIG. 4. It is assumed that the distribution ranges of the three parameters have been previously established for each particle, and that this information is stored in a memory in the analyzer in the form of an array of discriminating-space elements, each defined by an incremental area $\Delta I_t \times \Delta A_O$ and the associated intensity distributions of depolarized scattered light characteristic of the different particles types within that element.

As each particle passes through the one or more sensing zones, in the flow chamber, its optical scattering/absorption features are measured by the corresponding optical or non-optical detectors in the cytometer, which supply the response data in the form of voltage signals to the analyzer. The analyzer contains an analog-to-digital converter (ADC) (not shown) which converts the input voltage signals to digital $I_d$, $I_t$ and $A_O$ values. The $I_t$ and $A_O$ values form an ordered pair which is then identified with on of the discriminating-space volume elements, as being within the $\Delta I_t \times \Delta A_O$ area of that element. Once the corresponding volume element has been located, the measured $I_d$ value is compared with the distribution of $I_d$ values for particle A in that volume element. If the measured value is within the A particle $I_d$ range, the particle is classified as an A particle, and this information is recorded and/or supplied to a cell sorter in the cytometer, for purposes of separating A and B particles. Additionally, the quantified data may be plotted on a three-axis graph, as in FIG. 4, for displaying the density of cells in the feature space, and the cells may be counted.

If the particle $I_d$ value is not within the A particle range, in the associated discriminating space, but is within the B range, the particle is so classified, and this information is likewise stored, supplied to a sorter, and/or displayed. Similarly, the particle may be classified as neither A nor B, and so analyzed (which may involve storing or plotting particle type and/or counting or sorting the particles). After particle analysis, the analyzer is returned to a condition for processing parameter data from the next particle seen in the sensing zone. It will be appreciated how the algorithm can be modified for operation in a feature space having other than 3 dimensions.

The analyzer includes the above-mentioned ADC, a memory for data storage, and a microprocesser for locating, on the basis of measured input $I_t$ and A values, an appropriate discrimination space volume element, and for classifying particle type, based on the $I_d$ values within the identified volume element. The microprocesser may be a conventional design, and programmed for carrying out the above data storage and classification operations, according to conventional programming operations.

II. Operation

This section describes the theory of depolarized light scattering, as it is utilized in the present invention for particle discrimination (Part A), and exemplary cell-discrimination methods and results (Part B).

A. Theoretical Considerations

Figure 6:
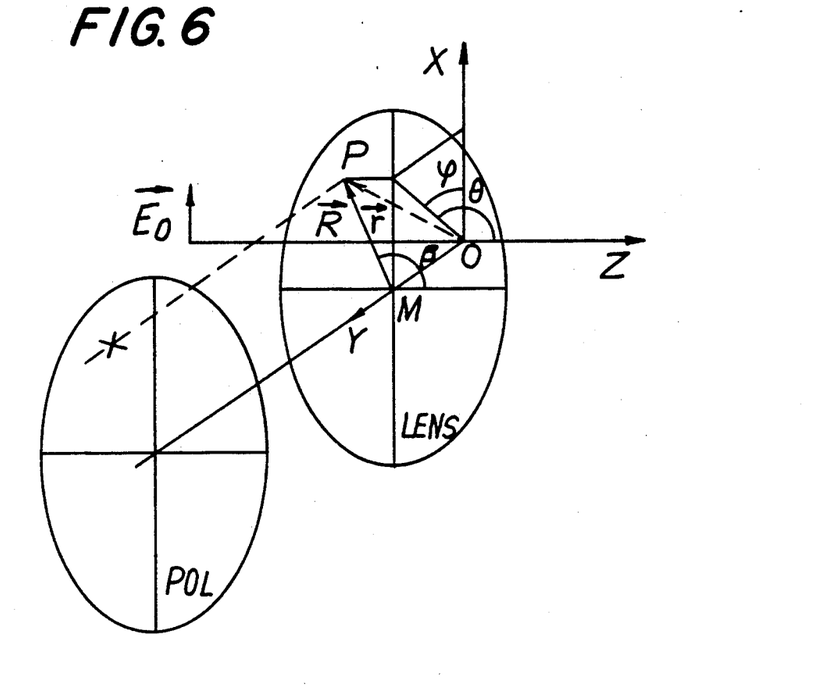
FIG. 6 is illustrates orthogonal light scattering from a single point at the origin O in the figure, where the propagation of scattered light is described by polar coordinates r, $\theta$ and $\phi$.

FIG. 6 illustrates the optical arrangement shown in FIG. 1 for orthogonal light scattering. An incoming laser beam propagates along the z-axis and is linearly polarized with incident electrical field E along the x-axis. At the origin O of our coordinate system the laser beam intersects the particles of the flow cytometer moving along the x-axis. The direction of the scattered light is described with spherical coordinates r, $\theta$ and $\phi$. The amplitudes of the scattered light, polarized in the $\theta$ and $\phi$ direction can now be described as (van de Hulst):

$$E_\phi = (S_4 \cos\phi - S_1 \sin\phi) f E_O \quad (1)$$

$$E_{74} = (S_2 \cos\phi - S_3 \sin\phi) f E_O \quad (2)$$

where f is a complex expression for a spherical wave, inversely proportional to r, the distance between the scatterer and the detector, and $S_1$, $S_2$, $S_3$ and $S_4$ are the so-called amplitude functions (van de Hulst) dependent on $\phi$, $\theta$ and the geometry and physical composition of the scatterer. The measurable light scattering intensities $I_\phi$ and $I_\theta$ are related to these fields by:

$$I_\phi = |E_\phi|^2 \quad (3)$$

$$I_\theta = |E_\theta|^2 \quad (4)$$

The light intensities measured using ideal polarizers transmitting only the x polarized or the z polarized fields, are called $I_l$ (for parallel) and $I_r$ (for perpendicular), respectively. $I_r$ is called the depolarized light scattering intensity and the depolarization ratio is defined here as:

$$D = \frac{I_r}{I_r + I_l} \quad (5)$$

For light scattered in the yz plane, i.e., orthogonal with respect to the polarization direction of the incident light, $\phi = 90°$ $I_l$ and $I_r$ can be written in the form:

$$I_1 = |S_1 f E_O|^2$$

$$I_r = |S_3 f E_O| \quad (6)$$

Thus, whereas $I_1$ is determined by $S_l$, measurement of the depolarized light scattering intensity in this geometry yields information on the term $S_3$. The importance of this term will be illustrated briefly.

Figure 7:
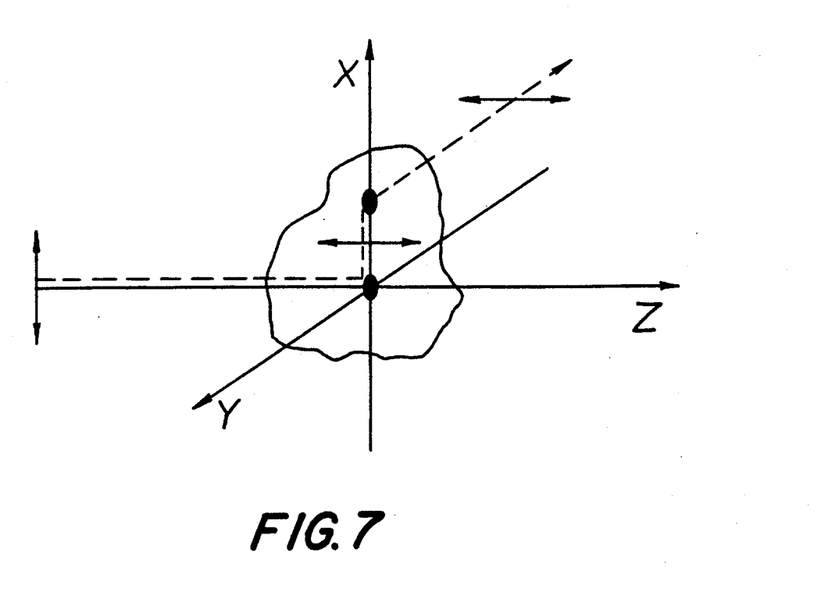
FIG. 7 shows an incident light ray as it is reflected by two intracellular particles, yielding a scattered ray propagating along the negative y-axis which is completely polarized in the z-direction.

For homogeneous spheres, spherical shells etc., the term $S_2$ is zero (van de Hulst), $S_3$ becomes important for particles which are optically anisotropic (due to shape and/or composition) and for particles containing structures so that multiple scattering becomes important. A simple, but striking example of the latter is illustrated in FIG. 7. Here the particle (cell) being illuminated contains two intracellular spheres located on the x-axis. A particular incoming ray, traveling along the z-axis, is reflected along the x-axis by the first sphere and along the y-axis by the second sphere. Applying the laws of reflection we find that the polarization direction of this ray changes from along the x-axis to along the z-axis. Thus it is seen how multiple reflections can lead to depolarization and thus contributions to the term $S_3$. In a similar way it can be shown that multiple scattering due to diffraction and refraction can also lead to depolarization. The multiple granular or other particulate material which can cause multiple scattering within a particle, and other particle structures, such as non-spherical shape, which can cause anisotropic light scattering, are referred to collectively herein as depolarizing structure.

Although the treatment of the above amplitude equations is simpler in the cases where $\Delta\phi$ equals 0° or 90° (forward or orthogonal scattering, respectively), it will be appreciated from FIG. 7 that particle depolarizing structures within a cell will produce depolarized scattered light at virtually all scattered angles. For example, a third intracellular particle in the cell illustrated in FIG. 7 could further reflect the depolarized light traveling along the y axis in either forward or backward scattering directions.

Typically, the optimal measuring angle for depolarized scattered light is the angle which gives best discrimination between the particles in the one dimensional ($I_d$) feature field. This, in turn, will depend on the relative amplitude functions of the different particle types. Of these, the most important are $S_3$ which dominates at orthogonal scattering angles, and $S_4$ which dominates at forward scattering. The relative contributions of these two terms can be assessed readily by depolarized light scattering measurements of the different particles at forward and orthogonal angles.

The discrimination between particles, on the basis of different depolarizing structure, may be further enhanced by reducing the cone angle $\Delta\phi$ at which light intensity is measured by the photodetector. As indicated above, an optical detector, such as a photomultiplier, gathers light from a cone around the axis at the selected measuring angle. In the case of orthogonal depolarized light scattering, this means that depolarization effects are caused not only by $S_3$ (the only term at 90°), but also by the other amplitude functions $S_1$, $S_2$ and $S_4$. This extra depolarization is due to the geometry of the measuring system and called cross depolarization. It is closely related to the term "aperture polarization" used when describing fluorescence polarization experiments.

Figure 8:
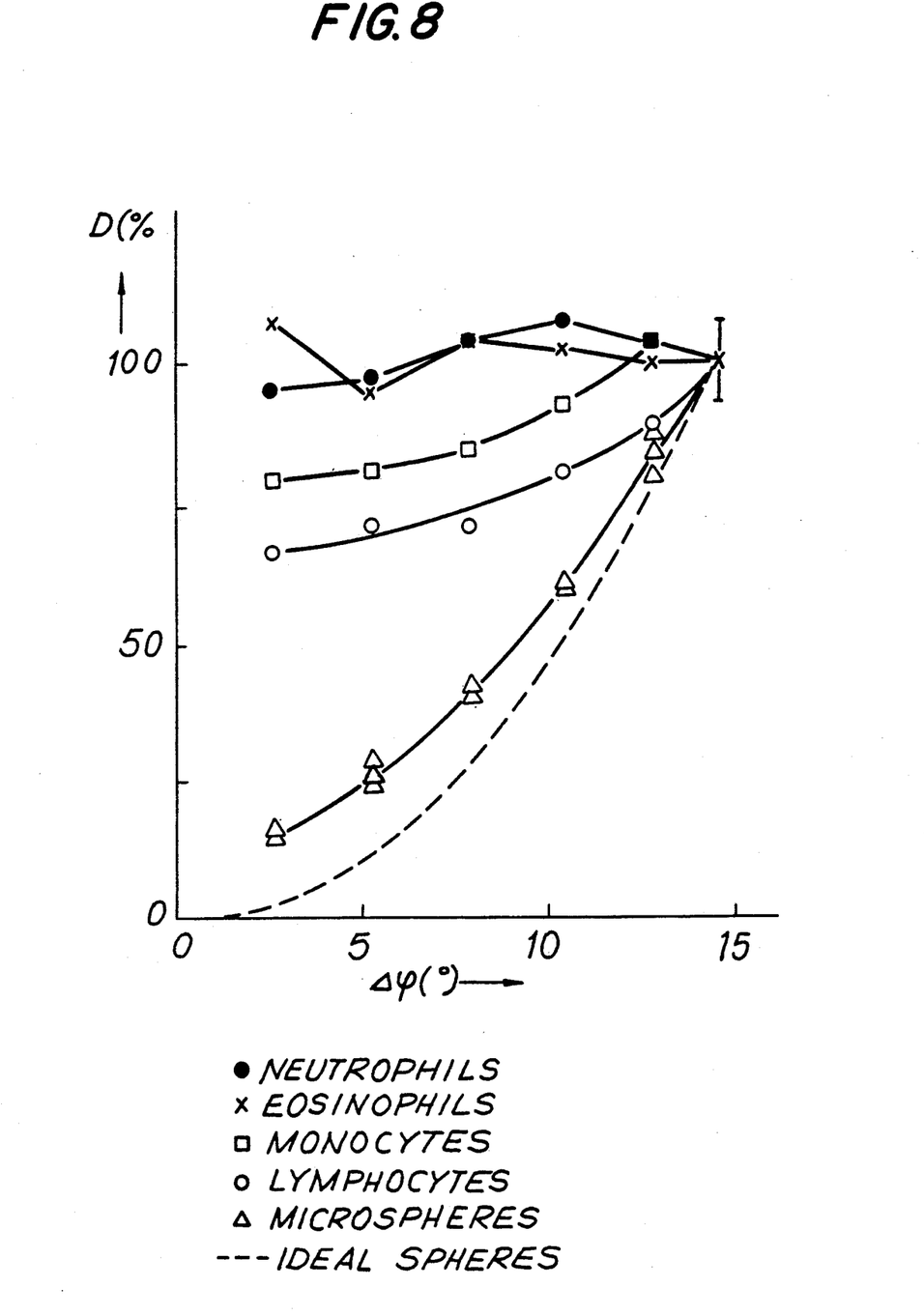
FIG. 8 shows flow cytometric density maps of total orthogonal light scattering versus depolarized orthogonal light scattering of different human blood cells.

The contribution of cross polarization to the depolarization effects measured at 90° can be determined by analyzing the dependence of the depolarization ratio on the cone angle $\phi$. This can be done by placing a rectangular diaphragm in front of the collection lens, (lens 42 in FIG. 1) limiting the angles of the collected light between $\phi = 90 \pm \Delta\theta$. In one study conducted in support of the invention, the measured depolarization intensity of a variety of different cell and particle types, as a function of acceptance angle, was examined. With reference to FIG. 8, the particles studied were: neutrophils (closed circles), eosinophils (crosses), monocytes (open squares), lymphocytes (open circles), and polystyrene microspheres having an average diameter of about 1.16 $\mu$ (open triangles). Orthogonal depolarized light scattering intensity was measured at cone angles $\Delta\phi$ of 2.5° and 14.5°. The results are shown in Table 1.

TABLE 1

|  | $\Delta\Phi = 2.5°$ | $\Delta\Phi = 14.5°$ |
| --- | --- | --- |
| Eosinophilic granulocytes | 4.7 | 4.4 |
| Neutrophilic granulocytes | 1.3 | 1.3 |
| Monocytes | 0.5 | 0.7 |
| Lymphocytes | 0.5 | 0.8 |

TABLE 1-continued

|  | $\Delta\Phi = 2.5°$ | $\Delta\Phi = 14.5°$ |
| --- | --- | --- |
| Microspheres | 0.62 | 3.9 |

As seen, cross polarization effects, as determined by the dependence of depolarization on acceptance angle, are largely absent in cells which are rich in internal granular structures (eosinophilic and neutrophilic granulocytes), very pronounced on spherical particles (microspheres) which presumably scatter light isotropically ($S_3 = S_4 = 0$), and intermediate for monocytes and lymphocytes which do not have pronounced internal granular structures.

The dependence of depolarized scattering intensity on cone angle was also studied at intermediate cone angles, with the results seen in FIG. 8. The curves in the figure have all been normalized to a common value at 14.5°. The dotted line in the figure is the theoretical second order dependence on acceptance angle calculated for ideal spheres. The results support the general conclusion from above that cells with highly polarizing (e.g., granular) structures show little cross polarization effects, while those with only moderate depolarizing structures are subject to cross polarizing effects. The results indicate that intensity distribution differences between highly and moderately depolarizing particles can be enhanced by performing orthogonal intensity measurements at a low conus angle.

If the different particles in a suspension are found to have overlapping depolarized intensity distribution ranges at both orthogonal and forward light scattering angles, and at low conus angles, one or more additional particle parameters will be required for particle discrimination. The simplest parameters are light scattering measurements, since these do not require additional light sources and/or flow cell modifications. One general type of light scattering measurement is depolarized light scattering at a second angle. This approach can be useful, for example, if the particles to be distinguished had different $S_3$ and $S_4$ values, such that the combination of orthogonal and forward depolarized scattering measurements gave distinct particle regions. A second type of scattering measurement is total scattered light, measured either at the same or a different angle as the depolarized scattered light. As will be illustrated below, this approach provides good separation of the feature space regions of different types of granulocytes. Finally, depolarized scattered light can be collected at different conus angles.

B. Applications

From the foregoing, it will be appreciated that the present method is applicable to any flow cytometer application in which the particles to be distinguished have different depolarizing structures. One important application is in distinguishing different blood cells types present in a blood cell sample or cellular fractionate. The cell types to be distinguished can include granulocytes from other cell types, different types of granulocytes, lymphocytes from monocytes, and subclasses of specific white cells.

As an example of cell discrimination in the case of strongly depolarizing cells, the method has been used to discriminate granulocytic eosinophils and neutrophils. Human blood was obtained by venipuncture from healthy individuals. Heparin was used as anticoagulant (150 USP U sodium heparin/10 ml Venoject Terumo Europe NV). Purified granulocytes were obtained by density separation according to published methods (Terstappen, 1985). Cell suspensions were adjusted to a concentration of $1 \times 10^6$/ml in phosphate buffered saline (PBS) containing 0.005% sodium azide and 1% bovine serum albumin (BSA). Measurements were performed the same day to preserve cell viability.

Figure 9A:
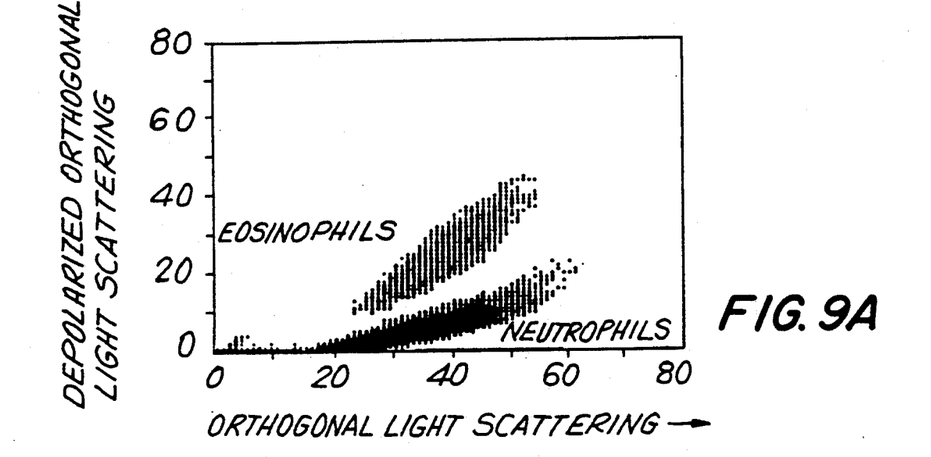
FIG. 9 is a plot of the depolarization ratio $D(\Delta\phi)/D(15°)$, where $D=(I_r/(I_r+I_l))$ measured as a function of the acceptance angle $\Delta\phi$ for neutrophyis (o), eosinophils (x), lymphocytes (o), monocytes (□) and microspheres with a diameter of 1.16 $\mu$ (Δ), where the dashed line represents the theoretical curve for ideal spheres.

Flow cytometric experiments were carried out with the flow cytometer described above, where the laser illuminating beam was set at 488 nm, and the scattering occurred in a 250 $\mu$m $\times$ 250 $\mu$m square flow channel. Orthogonal depolarized and total light scattering intensity were measured with the split beam configuration shown in FIG. 1. The results, displayed as a two-parameter density map, are shown in FIG. 9A. As seen, the method maps the two cell types into distinct and non-overlapping features regions, such as described in FIG. 3.

Since the intensity of the depolarized orthogonal light scattering is not high, the possibility that the measured depolarized light was due to elastic light scattering and not caused by autofluorescence was investigated. This was done by inserting a 500 nm shortwave pass filter in the detection optic; it did not affect the results. In addition, the illumination wavelength of the argon ion laser used was changed from 488 to 509 and 514 nm, and a helium neon laser of 633 nm was used. In all cases, the results obtained were the same.

The method was also applied to a cell-sorting operation, to separate the two populations of granulocytes. Here the flow cytometer was equipped with a conventional sorter, and the analyzer was designed to signal the sorter on the basis of rapid cell discrimination. The sorted granulocyte subpopulations were examined by light microscopy after May-Gruenwald staining. The cells with a relatively high depolarization of orthogonal light scattering were identified as eosinophilic granulocytes (99% purity) whereas the other population consisted of neutrophilic granulocytes (99% purity).

Figure 9B:
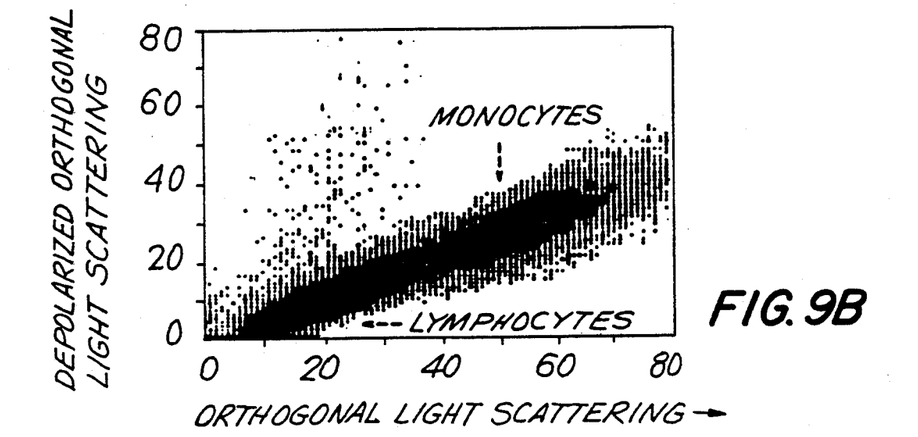

As an example of cell discrimination in the case of moderately depolarizing cells, the method has been used to discriminate lymphocytes and monocytes. Heparinized blood was obtained as above. Human leukocyte preparations were obtained by adding 190 ml of lysing buffer (8.29 g/l NH$_4$Cl, 0.0037 g/l Na$_2$ EDTA, 1.00 g/l KHCO$_3$) to 10 ml of whole blood and incubated for 20 minutes at 4° C. The lysed blood suspension was washed three times in PBS. Cell suspensions were adjusted to a concentration of $1 \times 10^6$/ml in PBS containing 0.005% sodium azide and 1% bovine serum albumin (BSA). Depolarized and total scattered light were measured as above. The results, displayed as a two-parameter density map, are shown in FIG. 9B. As seen, the method maps the two cell types into distinct and non-overlapping features regions. The density map also indicates the presence of a minor subpopulation of lymphocytes with relatively large depolarization.

Figure 9C:
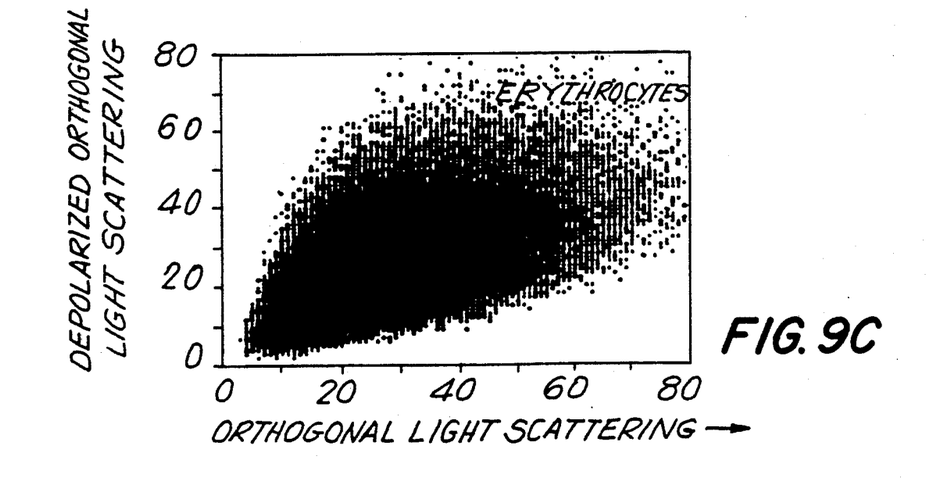

Human erythrocytes were also examined by the same method, with the results shown in FIG. 9C. The cells show little or no heterogeneity based on depolarization structure.

A variety of other cell types and non-cellular particles may also be distinguished and/or sorted according to the method of the invention. These include sperm cells, which have highly anisotropic structures, bacteria, on the basis of anisotropic shape, and crystalline particles, such as uric acid crystals, based on irregular crystal shape. For each of these particle types, optimal depolarization measurement conditions can be determined as above, and, if needed, additional optical and/or non-optical parameters can be selected according to the known behavior of the particle types to various optical- and/or non-optical-response properties of the particles.

From the foregoing, it can be appreciated how various objects and features of the invention are met. The method expands the types of particles which can be distinguished and/or sorted from one another, based on the different depolarization structure of the particles. In many cases, the depolarized orthogonal light scattering adds a very cost effective parameter to existing flow cytometers, and this simple addition can provide useful information, not available by other means.

As one example, the ability to distinguish eosinophilic granulocytes from neutrophilic granulocytes is of practical as well as of theoretical importance. It is now feasible to construct a simple flow cytometer provided with a low power laser, which can perform white blood cell differentiation with unstained cells. Heretofore, additional complex and unstable staining procedures had to be applied, or the weak autofluorescence had to be measured with an expensive argon ion laser (Weil).

While the invention has been described with reference to particular embodiments and applications, it will be appreciated that various other embodiments and applications based on the teaching of the present invention are possible.

What is claimed is:

1. A method of distinguishing and characterizing at least two distinct types of particles which have different depolarizing structures, said method comprising, directing a suspension of particles containing the distinct particle types through an optical sensing zone, illuminating the particles in the zone with an incident beam of linearly polarized light, by said illuminating, producing from each of the distinct types of particles, depolarized scattered light whose intensity, at a selected scattering angle, is dependent on the particle's depolarizing structure, and is within an intensity distribution range which is (a) characteristic of one of the particle types and (b) substantially non-overlapping with the intensity distribution of the other particle types in the suspension, in a particle-feature space which is defined in one dimension by depolarized light scattering intensity measured at the selected angle, measuring the intensity of the depolarized scattered light from each particle at the selected angle, and based on the intensity of the measured scattered light in the particle-feature space, distinguishing and characterizing at least two distinct particle types in the suspension.

2. The method of claim 1, wherein said illuminating is done with a beam of coherent linearly polarized light.

3. The method of claim 1, wherein the selected angle is orthogonal to incident light beam.

4. The method of claim 1, wherein the particle-feature space is a two-dimensional space which is defined in the second dimension, by a second light-intensity measurement whose mean values differ for the two different particle types.

5. The method of claim 4, wherein the second dimension is defined by the intensity of polarized scattered light measured at a selected angle.

6. The method of claim 5, for distinguishing eosinophils and neutrophils, wherein the depolarized light scattering intensity is measured at an angle which is approximately orthogonal to direction of the light beam.

7. The method of claim 6, wherein the polarized light scattering intensity is also measured at an angle which is approximately orthogonal to direction of the light beam.

8. The method of claim 7, wherein the particle-feature space is a three-dimensional space defined in the second and third dimensions, by the intensity of polarized light scattered from the illuminated particles, in directions which are substantially orthogonal and parallel to the incident light beam, respectively.

9. The method of claim 4, wherein the different particles have different wavelength-specific coefficients of extinction, and the second dimension is defined by the intensity of light in a forward direction due to wavelength-specific light absorption.

10. The method of claim 4, for discriminating particles having different intrinsic depolarization, wherein the depolarized scattered light is measured at, two different acceptance angles.

* * * * *